United States Patent [19]

Bayer et al.

[11] Patent Number: 5,030,759
[45] Date of Patent: Jul. 9, 1991

[54] SELECTIVE N-ALKYLATION OF ANILINE IN THE PRESENCE OF ZEOLITE CATALYSTS

[75] Inventors: Arthur C. Bayer, Ocean Springs, Miss.; Charles U. Pittman, Jr., Tuscaloosa, Ala.; Lichang Wang, Guangzhou, China; Earl G. Alley, Starkville, Miss.; Anthony C. Maliyackel, Cincinnati, Ohio

[73] Assignee: First Chemical Corporation, Pascagoula, Miss.

[21] Appl. No.: 343,818

[22] Filed: Apr. 27, 1989

[51] Int. Cl.$^5$ ............................................ C07C 209/28
[52] U.S. Cl. ................................... 564/401; 564/395
[58] Field of Search ........................................ 564/401

[56] References Cited

U.S. PATENT DOCUMENTS

| 4,602,112 | 7/1986 | Gier et al. | 564/474 |
| 4,737,592 | 4/1988 | Abrams et al. | 564/474 |
| 4,801,752 | 1/1989 | Chen et al. | 564/401 |
| 4,806,689 | 2/1989 | Gier et al. | 564/474 |

*Primary Examiner*—Glennon H. Hollrah
*Assistant Examiner*—Susan P. Treanor
*Attorney, Agent, or Firm*—Breiner & Breiner

[57] ABSTRACT

The selective N-alkylation of anilines comprising providing a mixture of a lower alkanol and an aniline, exposing said mixture to a temperature of from 250° C. to 350° C. in the presence of an acidic zeolite having a pore size of from 6 to 8 angstroms with a three-dimensional tubular shape, such as S-115 zeolite, is described. These zeolites are predominantly selective to the formation of N-alkylanilines.

11 Claims, 1 Drawing Sheet

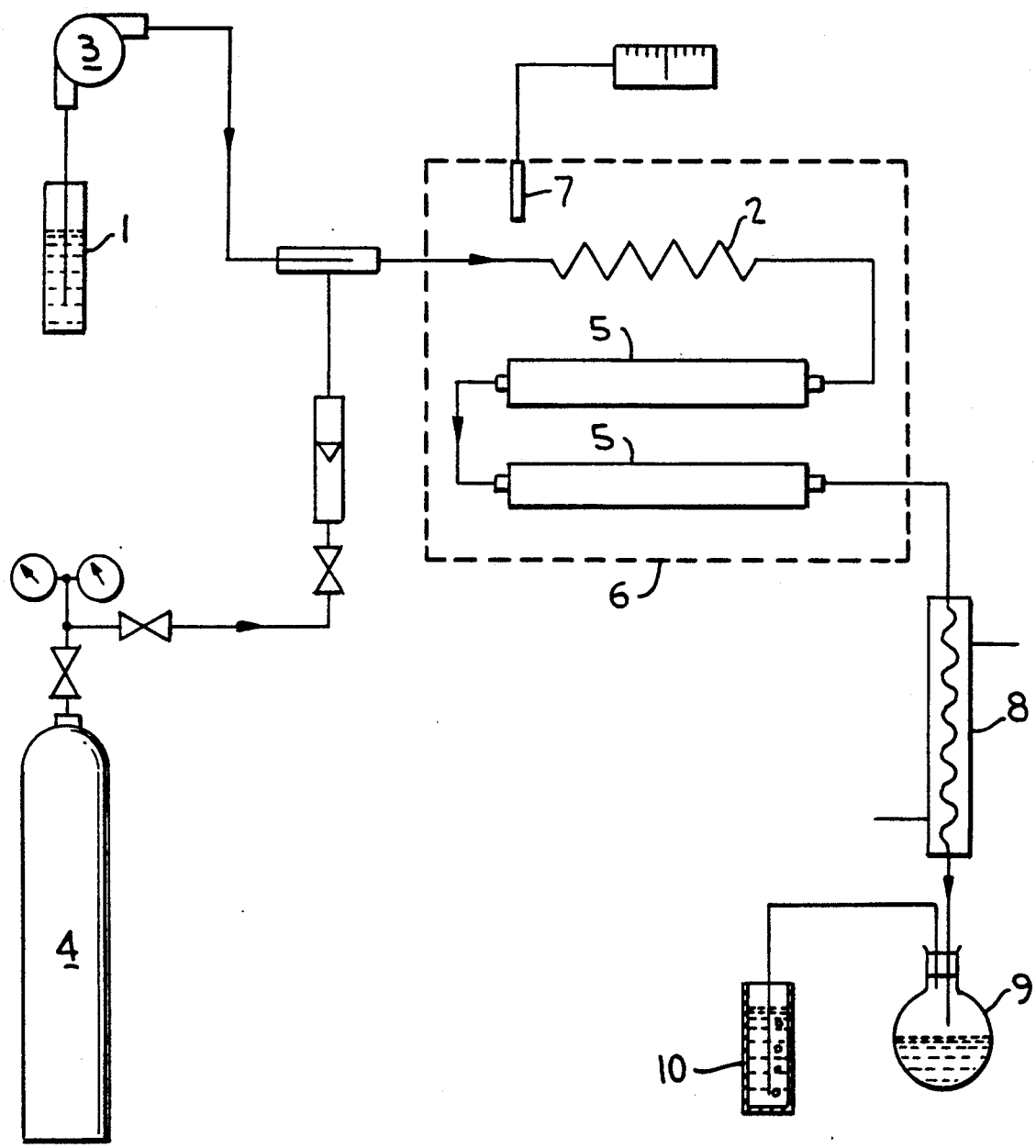

SELECTIVE N-ALKYLATION OF ANILINE IN THE PRESENCE OF ZEOLITE CATALYSTS

FIELD OF INVENTION

This invention relates to the selective alkylation of aniline in the presence of a zeolite. More particularly, the invention relates to the selective "N" alkylation of aniline to provide N-alkylaniline in the presence of a select zeolite catalyst. N-alkylation refers to the introduction of the alkyl group into the amino moiety of the aniline molecule. C-alkylation refers to the addition of the alkyl group onto a carbon atom of the benzene ring of the aniline molecule. The reactions of this invention can be carried out in the gas or liquid phase.

BACKGROUND OF INVENTION

Aniline alkylation for the introduction of an alkyl group onto the amino group of the aniline molecule, referred to as N-alkylation, or the addition of an alkyl group onto a carbon atom of the benzene ring, referred to as C-alkylation, has been extensively studied in that it is recognized that significant changes in the chemical and physical properties of aniline can be brought about by such alkylation. The alkylated compounds such as N-alkyl and N,N-dialkylaniline are useful in a variety of applications such as dyes, pharmaceuticals, anti-oxidants, plasticizers, herbicides, insecticides, plant growth agents, and vulcanization accelerators. A critical concern, however, in the alkylation of aniline is the selective production of specifically desired compounds. The different products of a mixture of products which are commonly formed during an alkylation reaction of aniline have very close physical constants such as boiling point, leading to difficulty in separation by conventional methods, such as distillation. In order to avoid the difficult and expensive separation or isolation of the components of a mixture, attempts have been made to provide selective alkylation processes.

It has been recognized in the prior art that the use of zeolites offer a convenient means of providing reaction selectivity. Thus, U.S. Pat. No. 4,274,982 discloses zeolite catalysts useful in the selective alkylation of aromatic molecules, and in particular to a method of maintaining the high para-selectivity of zeolite catalysts. Examples of alkyl aromatics produced utilizing the zeolite catalyst are the dialkylbenzenes. The useful life of a para-selective zeolite catalyst is prolonged by (1) maintaining the zeolite catalyst at a temperature of at least 50° C. or in an atmosphere substantially free of moisture; and (2) modifying the catalyst with at least 0.25% by weight of one or more difficulty reducible oxides. Additionally, the zeolite catalyst has a particular silica to aluminum ratio and constraint index.

Japanese Patent No. 53-28128 discloses anilines which are p-methylated by vapor phase contact of anilines with methanol in the presence of an alkali metal form of synthetic, and specifically a Y-type molecular sieve, zeolite catalyst to produce 2,4-xylidine.

U.S. Pat. No. 4,593,124 discloses, inter alia, a process for preparing an isomeric mixture of an alkyl substituted aniline by contacting at least one isomer of the alkyl substituted aniline with a zeolite catalyst.

U.S. Pat. No. 4,480,128 discloses, inter alia, a process for the manufacture of at least one of the ortho-, meta, or para-toluidine compounds by treating a first charge containing at least one toluidine isomer with an isomerization catalyst and then isolating the desired isomer by selective adsorption to a zeolite catalyst. The isomerization catalyst or may be a synthetic zeolite of the pentasil type or an X or Y type zeolite. The patent discloses that the isomerization reaction can be carried out in the gas phase and that the catalyst can be fixed. The isomerization reaction is stated as proceeding in a very selective manner.

U.S. Pat. No. 4,554,380, a continuation of U.S. Pat. No. 4,480,128, discloses a method for making at least one of the ortho, meta, or para-toluidine compounds by contacting at least one of the toluidine isomers, other than the isomer(s) sought to be isolated, with an isomerization catalyst which is a synthetic zeolite of the pentasil type.

European Patent No. 92,103, as discussed in Chemical Abstracts, Vol. 100, paragraph 605d, and U.S. Pat. No. 4,593,124, discloses individual toluidine isomers prepared by isomerizing isomer mixtures or pure undesired toluidine isomers over a pentasil type zeolite. The desired isomer is then separated by adsorption on a average to large pore size zeolite catalyst.

U.S. Pat. No. 3,868,420 disclosed, inter alia, the production of a phenylamine alkylated in the ortho- and/or para-positions by alkyl groups comprising the steps of reacting the phenylamine with an alkanol in the vapor phase in the presence of an aluminum oxide/molybdenum oxide mixed catalyst.

U.S. Pat. No. 4,613,705 discloses, inter alia, the alkylation of aromatic amines with an alkanol in the presence of a mixed metal oxide alkylation catalyst consisting of at least 70% by weight of a Group V-B metal oxide and 30% by weight of stannic oxide. The patent discloses as prior art an article appearing in *Waseda Daigaku Rikogaku Kenkyusho Hokoku* by Takamiya et al, Vol. 69, pp. 21-25 (1975), which is stated as reporting the results of a study of the vapor phase catalytic N-methylation of aniline with methanol with certain transition metal zeolites as catalysts.

U.S. Pat. No. 4,599,449 discloses, inter alia, a process for alkylating aromatic amines comprising reacting an aromatic amine with an alkanol in the presence of a metal oxide alkylation catalyst consisting essentially of at least 70 mole percent of a Group VII-B metal oxide and no more than about 30 mole percent of a Group VIII metal oxide.

U.S. Pat. No. 4,582,936 discloses, inter alia, the production of a dimethyl amine by the gas phase reaction of ammonia and methanol over a zeolite catalyst. The patent discloses as prior art that various zeolites have come of interest in producing a specific amine, such as monomethyl amine or dimethyl amine, with high selectivity. Japanese Patent Publication No. 113747/1981 is referred to in the patent as disclosing a method for selectively obtaining the monomethyl amine from ammonia and methanol utilizing various zeolites inclusive of mordenite.

U.S. Pat. No. 3,751,504 discloses, inter alia, a process for effecting vapor phase alkylation of an aromatic hydrocarbon charge by contacting the aromatic hydrocarbon charge with an alkylating agent in the presence of a catalyst characterized by a particular x-ray diffraction pattern. The catalyst claimed belongs to the family of zeolites known as Zeolite ZSM-5 stated to be suitable alkylating agents.

U.S. Pat. No. 3,751,506 discloses, inter alia, a process for effecting vapor phase alkylation of an aromatic hydrocarbon charge with an alkylating agent in the presence of a crystalline aluminum silicate zeolite having a specific formula under specific reaction conditions. The catalyst useful in the disclosed invention belongs to the family of zeolites known as Zeolite ZSM-5.

U.S. Pat. No. 3,755,483 discloses, inter alia, the process for effecting the vapor phase alkylation of a hydrocarbon charge with an alkylating agent in the presence of a zeolite catalyst having a specific x-ray diffraction pattern. The catalyst useful in the invention is known as Zeolite ZSM-12.

U.S. Pat. No. 4,613,717 discloses, inter alia, a process for producing a 1,4-dialkylbenzene comprising contacting benzene or a monoalkylbenzene with an alkylating agent in the vapor phase in the presence of a zeolite catalyst.

U.S. Pat. No. 3,598,878 discloses, inter alia, a process for the alkyl transfer of an alkyl aromatic comprising contacting an alkyl aromatic feed material with a catalyst comprising vanadium deposited on a zeolite base.

U.S. Pat. No. 3,597,491 discloses, inter alia, a process for the alkyl transfer of alkyl aromatics comprising contacting an alkyl aromatic feed material with a catalyst comprising a Group VI-B metal deposited on a type Y zeolite base.

U.S. Pat. No. 4,599,473 discloses, inter alia, a process for the selective alkylation of a monoalkylbenzene into a dialkylbenzene utilizing a silica catalyst of the silicalite type. The patent discloses as prior art that various alumino-silicate type zeolite catalysts, including those known as ZSM catalysts, are suitable for selectively producing para-substituted benzene derivatives upon being modified for that purpose. It is stated that one of the disadvantages of these catalysts is that they must often be modified with promoters to obtain significantly increased para-selectivity, i.e., that these types of catalysts have little or no intrinsic para-selectivity.

U.S. Pat. No. 4,548,914 discloses, inter alia, a method of enhancing the para-selectivity of a zeolite catalyst which is modified with one or more metal oxides in combination with phosphorus oxide. The patent discloses using the modified zeolite catalyst to produce the para-dialkylbenzene isomer.

U.S. Pat. No. 4,434,299 discloses, inter alia, a process for the production of aromatic amines by reaction of an alicyclic alcohol with ammonia in the presence of a catalyst wherein the catalyst is a crystalline silicate zeolite.

U.S. Pat. No. 3,231,616 discloses the production of aromatic amines, such as aniline, under continuous vapor phase operation by ammonolysis in presence of an aluminum silicate catalyst, broadly known as zeolite.

U.S. Pat. No. 3,251,897 discloses the alkylation of hydrocarbons or substituted hydrocarbons in the presence of a zeolite catalyst.

The article entitled "Alkylation on Synthetic Zeolites" by Yashima et al, *Journal of Catalysis*, Vol. 16, pp. 273–280 (1970), noted in U.S. Pat. No. 4,080,395, discusses the catalytic activity of zeolite Y during the alkylation reaction of toluene with methanol. The article concludes that p-xylene can be selectively obtained using highly active zeolite catalysts.

The article entitled "Alkylation on Synthetic Zeolites" by Yashima et al, *Journal of Catalysis*, Vol. 26, pp. 303–312 (1972), noted in U.S. Pat. No. 4,115,424, discusses the alkylation of toluene with methanol and formaldehyde on alkali cation exchanged zeolites.

The article entitled "Industrial Application of Shape-Selective Catalysis" by N. Y. Chen and W. E. Garwood, *Catal. Rev.-Sci. Eng.*, 28 (2&3), 185–264 (1986), discloses, inter alia, shaped selective catalysis based on zeolites including with respect to obtaining para-selective reactions.

Additional patents which disclose the production of a hydrocarbon, such as dialkylbenzene, utilizing a modified zeolite catalyst having high-para-selectivity are as follows:

| | | | |
|---|---|---|---|
| 3,728,408 | 4,275,256 | 4,469,806 | 4,478,949 |
| 4,007,231 | 4,370,508 | 4,472,518 | 4,486,616 |
| 4,080,395 | 4,391,739 | 4,477,583 | 4,532,226 |
| 4,080,396 | 4,391,998 | 4,477,584 | 4,581,215 |
| 4,090,981 | 4,409,132 | 4,477,585 | 4,593,137 |

None of this latter group of patents specifically discloses the zeolite containing catalyst as suitable for use in connection with an amine.

Accordingly, zeolites as apparent from the hereinbefore noted patents and literature publications have been found to have activity for a variety of reactions, particularly the carbonium reaction. The source of carbonium-ion activity in the zeolite is believed to reside in the acidic characteristics of the structure. Zeolite acidity, in turn, depends on the nature of cation present, the extent of ion exchanged, the Si/Al ratio of the lattice, the heat treatment of the zeolite, and the amount of water present. This acidity is believed to be constituted by both Bronsted acids and Lewis acids. The reaction selectivity of the zeolites is believed to be due, at least in major part, to the three-dimensional framework of silica and alumina tetrahedra. This framework, as recognized in the art, can take many different configurations depending on how the tetrahedra are arranged and joined together and how much $AlO_4$ is substituted for $SiO_4$. The tetrahedra are arranged so that sizable cavities, channels, or cages exist within the structure. This framework or shape can be adjusted to fit different size molecules of reactants, products, or intermediates. The catalytic behavior of zeolites, including their selectivity, is applicable to both vapor-phase and liquid-phase reactions of different kinds of hydrocarbons and their derivatives.

Although there has been extensive activity with respect to the use of zeolites for selective reactions, no one to date has used the zeolites for the selective N-alkylation of aniline with lower alkanols, or recognized the temperature dependence of such reactions.

SUMMARY OF INVENTION

The present invention provides for the selective alkylation of aniline with a lower alkanol in the presence of specific zeolite catalysts are controlled temperatures to selectively provide N-alkylaniline or N,N-dialkylaniline. Thus, according to the invention, aniline is reacted with a lower alkanol in the presence of a synthetic, small pore zeolite, such as Union Carbide's S-115, at controlled temperatures, to selectively provide N-alkylaniline, and, with continuation of the reaction, N,N-dialkylaniline, according to the mechanisms

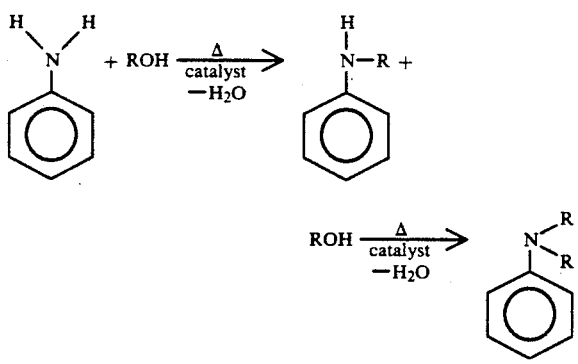

wherein R is methyl, ethyl, n-propyl, isopropyl, or n-butanol, collectively defined herein as lower alkyl groups. These products obtained in high yields can be utilized as such or further reacted with aniline to give para-alkylaniline as disclosed in our concurrently filed and commonly assigned application entitled "Selective C-Alkylation of Aniline in the Presence of Zeolite Catalysts to Para-aniline," U.S. Ser. No. 07/343,876.

The reaction conditions of the alkylation of aniline, in addition to temperature, are instrumental in the selectivity of the alkylation products obtained. It has been found that temperatures within the range of about 250° C. to 350° C. are critical to selective N-alkylation of aniline in the presence of the select zeolites. Higher temperatures lead to C-alkylation or formation of product mixtures. Further, maintaining a high aniline ratio at the reaction site suppresses the formation of the di- and tri-alkylated compounds. With high flow rates where the contact time of reactants with catalyst is short, e.g., short residence time of the reactants on the catalyst bed, N-alkylaniline formation is favored. Further, zeolites of small particle size contribute to enhanced lifetime before regeneration of the zeolite catalysts is necessary.

The formation of N-methyl and dimethylaniline starting with methanol and aniline is the highly preferred embodiment of this invention.

THE DRAWING AND PREFERRED EMBODIMENTS

In the drawing the sole figure is a schematic illustration of an apparatus for use in the alkylation of aniline. Referring to the drawing, the reactants aniline and lower alkanol are mixed at the desired ratio and charged to vessel 1. The reaction mixture is fed from vessel 1 to a preheater 2 by a liquid chromagraphy pump 3. The preheater is also fitted for supply of a carrier gas such as nitrogen from a second line connected to a gas tank 4. Zeolite catalyst is placed in tube reactors 5. The preheaters and reactors are located in an oven 6 which is controlled by a thermocoupler 7 in the temperature range from room temperature to 500° C. The catalyst is calcined at a desired temperature for from two to four hours in a carrier gas stream. The reaction temperature is controlled in the range of 250° C. to 350° C. The products of alkylation are cooled with a condenser 8 and collected in a flask 9 attached to the condenser. A gas trap 10 is interconnected with flask 9.

The zeolites for use according to the present invention which are selective to N-alkylation of aniline are small-size port zeolites exemplified by Union Carbide's S-115 zeolite. These zeolites have pore diameters within the range of five to eight angstroms, with high pore selectivity, three-dimensional channels and a high silica to alumina content, with a typical oxygen capacity within the range of about 15 to 20 weight-percent of 183° C. and 100 torr pressure, with a surface area of about 400 to 600 m²/g. Certain properties of the S-115 zeolites in comparison to LZ-M, ELZ-Ω and LZ-Y zeolites are set forth in Tables 1-3.

TABLE 1

| | Comparative Zeolite Properties | | | | |
|---|---|---|---|---|---|
| Type | Pore Size (Å) | Pore Volume H₂O (cc/g) | Channels | Pore Selectivity | Si/Al |
| LZ-Y | 8–10 | 0.35 | 3D | Low | 2.4 |
| LZ-M | 8–10 | 0.21 | 1D | Moderate | 3 |
| ELZ-Ω | 8–10 | 0.21 | 1D | Moderate | 3.5 |
| S-115 | 6 | — | 3D | High | 300 |

1D means one dimensional
2D means two dimensional
3D means three dimensional

TABLE 2

| | Typical Acid Performance Characteristics For UCC Molecular Sieves Activated at 500° C. | | |
|---|---|---|---|
| Type | Butane* @ 500° C. | NH₃ ads (TGA) @ 200° C., mole/g | Pyridine ads (IR) @ 150° C., mole/g (Bronsted) |
| LZ-Y52 | 0.4 | 495 | — |
| LZ-Y62 | 1.4 | 3094 | 429 |
| LZ-Y72 | 0.5 | 1067 | 197 |
| LZ-Y82 | 30–36 | 2882 | 350 |
| LZ-Y20 | 1.8 | 475 | — |
| ELZ-Ω-6 | 101.1 | 1366 | — |
| LZ-M-6 | 167.5 | 2106 | 328 |
| S-115 | 1.8 | 169 | 12 |

*A method using n-butane cracking activity to measure the acid-type catalytic activity.

TABLE 3

| | Typical Oxygen Capacity and Surface Area Values for UCC Molecular Sieves | |
|---|---|---|
| Type | 0 Capacity, wt % (−183° C., 100 torr) | Surface Area, m²/gm (1 pt. BET, N₂) |
| LZ-Y52 | 33.6 | 886 |
| LZ-Y62 | 34.0 | 889 |
| LZ-Y72 | 28.8 | 725 |
| LZ-Y82 | 29.0 | 760 |
| LZ-Y20 | 23.3 | 611 |
| ELZ-Ω-6 | 17.9 | 452 |
| LZ-M-6 | 17.0 | 530 |
| S-115 | 18.9 | 437 |

The S-115 zeolite catalysts provide virtually no C-alkylation at 300° C., with the main product, particularly with high aniline ratios, being N-alkylaniline. This high formation of methyl- and dimethylaniline with no C-alkylation is in contrast with other zeolites and particularly the Y-type zeolites as seen from Table 4.

TABLE 4

| Aniline Alkylation Over Different Zeolite Catalysts | |
|---|---|
| Reaction Conditions: | |
| Temperature | 300° C. |
| Reactant Ratio | 2:1 (mole) |
| Reaction Time | ~1 hour |
| Resident Time | 4.7 sec. |

TABLE 4-continued

Aniline Alkylation Over Different Zeolite Catalysts

| | Carrier Gas | | | N₂ 40 ml/min. | | | | |
|---|---|---|---|---|---|---|---|---|
| | Compositions (mole %) | | | | | | | |
| Compounds in Products | S-115 (6 Å) 3D | LZ-M-6 (8–10 Å) 1D | ELZ-Ω-6 (8–10 Å) 1D | LZ-Y20 (8–10 Å) 3D | LZ-Y52 (8–10 Å) 3D | LZ-Y62 (8–10 Å) 3D | LZ-Y72 (8–10 Å) 3D | LZ-Y82 (8–10 Å) 3D |
| Aniline | 65.2 | 86.4 | 74.3 | 64.6 | 79.1 | 70.8 | 60.7 | 59.9 |
| N-MA | 27.9 | 11.8 | 20.4 | 10.6 | 19.0 | 24.0 | 3.8 | 2.0 |
| o-tol | — | — | — | 0.7 | — | — | 0.7 | 1.2 |
| p-tol | — | 1.0 | 2.3 | 18.4 | — | 1.9 | 31.8 | 33.6 |
| m-tol | — | — | — | — | — | — | — | — |
| N,N-DMA | 4.9 | 0.8 | 2.2 | 0.7 | 1.9 | 3.3 | — | — |
| N-MPT | — | — | — | — | — | — | 1.6 | 0.9 |
| 2,4-DMA | — | — | 0.9 | 2.0 | — | — | 1.3 | 2.4 |
| 2,4,6-TMA | — | — | — | — | — | — | — | — |
| Unknown | 2.0 | — | — | — | — | — | — | — |
| o/p | 0/0 | 0/1.0 | 0/2.2 | 1/26.3 | 0/0 | 0/1.9 | 1/45.4 | 1/28 |
| N-mono/N,N-di | 5.7/1 | 14.8/1 | 9.4/1 | 16.4/1 | 10/1 | 7.3/1 | 3.8/0 | 2.0/0 |

As apparent from Table 4, S-115, LZ-M-6 and ELZ-Ω-6 zeolites at 300° C. favor the formation of N-methylaniline. However, the yield with LZ-M-6 and ELZ-Ω-6 is lower with some C-alkylation occurring. The LZ-Y20LZ-Y72 and LZ-Y82 zeolites at 300° C. favor the formation of C-alkylation; whereas LZ-Y52 and LZ-Y62 zeolites at 300° C. again favor the formation of the N-methylaniline, but again with relatively low yields. As temperature increases, the C-alkylation activity increases for all the Y-zeolites but not for S-115. Moreover, at temperatures of 350° C. and above, C-alkylation of aniline to obtain para-selectivity is favored by all Y-type zeolites as is illustrated in Table 5.

TABLE 5

Aniline Alkylation Over Different Zeolite Catalysts

Reaction Conditions:
Temperature: 350° C.
Reactant Ratio: 2:1 (mole)
Reaction Time: ~1 hour
Resident Time: 4.4 sec.
Carrier Gas: N₂ 40 ml/min.

| | Compositions (mole %) | | | | | | | |
|---|---|---|---|---|---|---|---|---|
| Compounds in Products | S-115 (6 Å) 3D | LZ-M-6 (8–10 Å) 1D | ELZ-Ω-6 (8–10 Å) 1D | LZ-Y20 (8–10 Å) 3D | LZ-Y52 (8–10 Å) 3D | LZ-Y62 (8–10 Å) 3D | LZ-Y72 (8–10 Å) 3D | LZ-Y82 (8–10 Å) 3D |
| Aniline | 58.7 | 75.4 | 70.8 | 59.1 | 70.7 | 62.0 | 62.7 | 64.1 |
| N-MA | 32.3 | 20.1 | 10.9 | 1.3 | 3.7 | 1.1 | 1.4 | — |
| o-tol | — | — | 1.2 | 3.0 | 1.4 | 3.0 | 2.5 | 4.6 |
| p-tol | — | 2.4 | 14.0 | 27.1 | 22.7 | 31.3 | 30.8 | 28.1 |
| m-tol | — | — | — | — | — | — | — | — |
| N,N-DMA | 7.0 | 2.0 | 0.7 | 0 | — | — | — | — |
| N-MPT | 0.3 | — | 1.9 | 0.6 | 0.9 | — | 0.5 | — |
| 2,4-DMA | — | — | 0.6 | 4.7 | 0.7 | 2.6 | 2.1 | 3.2 |
| 2,4,6-TMA | — | — | — | 4.2 | — | — | — | — |
| Unknown | 1.7 | — | — | — | — | — | — | — |
| o/p | 0/0 | 0/2.4 | 1/11.8 | 1/9.0 | 1/16 | 1.10.4 | 1/12.3 | 1/6.1 |
| N-mono/N,N-di | 4.6/1 | 10.1/1 | 15.6/1 | 1.3/0 | 3.6/0 | 1.2/0 | 1.4/0 | 0/0 |

| Key to Abbreviations Used Herein | |
|---|---|
| N-MA | N-methylaniline |
| o-tol | ortho-methylaniline (ortho-toluidine) |
| p-tol | para-methylaniline (para-toluidine) |
| m-tol | meta-methylaniline (meta-toluidine) |
| N,N-DMA | N,N-dimethylaniline |
| N-MPT | N-methyl-para-toluidine |
| N,N-DMPT | N,N-dimethyl-para-toluidine |
| 2,4-DMA | 2,4-dimethylaniline |
| 2,4,6-TMA | 2,4,6-trimethylaniline |
| o/p | ratio of ortho to para isomer |
| o/p/m | ratio of ortho to para to meta isomer |
| N-mono/N,N-di | N-methyl to N,N-dimethyl aniline ratio |

As seen from Table 5, when the temperature is increased from 300° C. to 350° C., the amount of C-alkylation is increased when using all of the Y-type zeolites. However, with S-115 zeolites, the N-methylaniline and N,N-dimethylaniline remains high with no ring- or C-alkylation occurring.

As seen from Table 6, S-115 zeolite is selective to the formation of N-alkylanilines, with no ring-alkylation occurring up to 350° C. where some ring-alkylation will occur. Remarkably, even at 400° C. with S-115 zeolites only small amounts of C-alkylation are observed and selectivity to N-alkylation is high.

TABLE 6

Temperature Effect of Aniline Alkylation Over S-115

Reaction Conditions
Reactant Ratio: Aniline/MeOH = 2:1 (mole)
Reaction Time: ~1 hour
Carrier Gas: 40 ml/min.

| Compounds in Products | Compositions (mole %) | | | | |
|---|---|---|---|---|---|
| | 250° C. | 300° C. | 350° C. | 400° C. | 450° C. |
| Aniline | 87.2 | 65.2 | 58.7 | 61.4 | 71.1 |
| N-MA | 11.6 | 27.9 | 32.3 | 28.3 | 5.0 |
| o-tol | — | — | — | 1.3 | 7.9 |

TABLE 6-continued

Temperature Effect of Aniline Alkylation Over S-115

| | | | | | |
|---|---|---|---|---|---|
| p-tol | — | — | — | 2.8 | 6.2 |
| m-tol | — | — | — | — | 6.3 |
| N,N-DMA | 1.2 | 4.9 | 7.0 | 5.1 | — |
| N-MPT | — | — | 0.3 | 1.0 | — |
| N,N-DMPT | — | — | — | — | — |
| 2,4-DMA | — | — | — | — | 1.5 |
| 2,4,6-TMA | — | — | — | — | — |
| Unknown | — | — | 1.7 | — | 2.1 |
| o/p/m | 0/0/0 | 0/0/0 | 0/0/0 | 1/2.2/0 | 1/0.8/0.8 |
| N-mono/N,N-di | 9.6/1 | 5.7/1 | 4.6/1 | 5.5/1 | 5.0/0 |

It has been found that with lower aniline flow rates, i.e., longer residence times of reactants on the catalyst bed, the formation of N,N-dialkylaniline if favored. Also is higher alkanol/aniline feed ratios, the formation of N,N-dialkyl-anilines is favored. It is theorized that the smaller pore size zeolites, e.g., smaller than Y-zeolites, will permit the entrance of reactant aniline and lower alkanol, and will permit the easy exit of N-alkylaniline and N,N-dialkylaniline. Furthermore, the transition state where the bond between nitrogen and the carbon of alkanol is formed, to give the N-alkylated product, is readily accommodated within the S-115 internal pore structures. The transition state structure within zeolite pores for N-alkylation is believed to be

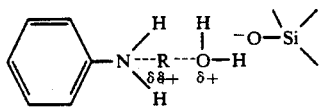

R = CH3 and other lower alkyl groups

The nitrogen of aniline forms a bond to the carbon of the alkanol which contains the —OH group. First, the —OH group is protonated by an acidic

site. As the C—O bond breaks, the N—C bond is formed. This transition state is substantially smaller than the bis-aryl transition states for "bimolecular" C-alkylation. The transition state required for ready C-alkylation, in the 300°–400° C. temperature range, involves a bis-aryl transition state that cannot fit within the S-115 pore and cavity structure. This bis-aryl transition state involves the transfer of an alkyl group from an N-alkylated aniline to the ring carbon of another aniline, or N-alkylated aniline, molecule. Only the larger "super-cavities" of the three-dimensional Y-zeolites can accommodate this transition state. Therefore, the S-115 zeolite is highly selective for N-alkylation.

It is surprising and unexpected that the temperature of the reaction plays such a major role in the N-alkylation or C-alkylation selectivity. In general, alkylation occurs in the temperature range of about 250° C. to 500°C., with N-alkylation occurring at the lower temperatures of from about 250° C. to about 350° C., and C-alkylation occurring at temperatures above about 300° C., and is most favored at from 350° C. to about 450° C.

It is also surprising and unexpected that at temperatures below about 350° C. no substantial C-alkylation occurred when using S-115 with only N-alkylanilines being produced. Accordingly, the selective N-alkylation of aniline is believed to be controlled by both the size and shape of the pores in the zeolite catalyst and by reaction temperature.

The N-alkylation reaction is dependent on the ratio on aniline to alkanol as illustrated in Table 7.

TABLE 7

Effect of the Reactant Ratio (Aniline/MeOH) In Aniline Alkylation Over S-115

| Reaction Conditions | | | | | | |
|---|---|---|---|---|---|---|
| Temperature | | | 350° C. | | | |
| Reaction Time | | | ~1 hour | | | |
| Carrier Gas | | | 40 ml/min. | | | |

| | Composition (mole %) | | | | | |
|---|---|---|---|---|---|---|
| Compounds | Ratio of Aniline/MeOH (mole) | | | | | |
| in Products* | .44/1 | .88/1 | 1.33/1 | 1.77/1 | 2.0/1 | 2.22/1 |
| Aniline | 15.9 | 26.8 | 49.8 | 52.9 | 59.7 | 65.2 |
| N-MA | 35.2 | 36.5 | 38.5 | 36.6 | 32.9 | 29.5 |
| o-tol | — | — | — | — | — | — |
| p-tol | — | — | — | — | — | — |
| m-tol | — | — | — | — | — | — |
| N,N-DMA | 45.7 | 31.0 | 11.7 | 10.1 | 7.1 | 5.3 |
| N-MPT | 0.8 | 2.1 | — | 0.4 | 0.3 | — |
| N,N-DMPT | 2.4 | 3.6 | — | — | — | — |
| 2,4-DMA | — | — | — | — | — | — |
| 2,4,6-TMA | — | — | — | — | — | — |
| Unknown | — | — | — | — | — | — |
| o/p | | | | | | |
| N-mono/ N,N-di | 0.77/1 | 1.18/1 | 3.29/1 | 3.62/1 | 4.63/1 | 5.57/1 |

*All the data in Table 7 was obtained from the samples collected after one-hour run.

Thus, increasing the ratio of aniline to lower alkanol leads to higher formation of N-alkylaniline with the formation of N,N-dialkyl and the tri-alkylated components being suppressed. Low ratios of aniline provides a very high yield of N,N-dialkylaniline. It has been determined that the reactive sites at the external surface of the zeolites play only a minor role in the reactive selectivity of the zeolite. The internal sites play the major role.

Flow rate also is a factor to a limited extent in the selective N-alklation of aniline. A low flow rate, which means a longer residence time, increases the N-alkylation of the aniline. It has been found that the residence time of reactants over the catalyst can effectively range from 0.1 to about 40 seconds.

According to the present invention, therefore, the selective control of zeolite and control of reaction temperature will promote N-alkylation of the aniline. Additionally, the selection of ratio of aniline to lower alkanol and flow rate are contributing factors to the formation of the desired N-alkylation selectivity.

A particularly significant advantage of the present invention is that the S-115 zeolite have a long lifetime in the process and, additionally, they can be reactivated by heating to a high temperature. The process of N-alkylation is, thus, relatively economical.

The experimental work reported above, for purposes of a control, has used methanol as the lower alcohol. However, substantial equivalent results are realized with ethyl alcohol, N-propylalcohol, isopropylalcohol, and n-butanol, collectively referred to herein as the lower alkanols.

As will be apparent to one skilled in the art, various modifications can be made within the scope of the aforesaid description. Such modifications being within the ability of one skilled in the art form a part of the present invention and are embraced by the appended claims.

It is claimed:

1. A process for the selective N-alkylation of anilines comprising providing a mixture of a lower alkanol and an aniline, exposing said mixture to a temperature of from 250° C. to 350° C. in the presence of an acidic zeolite having a pore size of from about 6 to 8 angstroms and channels with three-dimensional a tubular shape; and recovering said N-alkylation reaction products.

2. The process of claim 1 wherein said temperature is within the range of from about 300° C. to 350° C.

3. The process of claim 1 or 2 wherein the process is carried out in the vapor phase.

4. The process of claim 1 or 2 wherein the process is carried out in the liquid phase.

5. The process of claim 1 or 2 wherein said lower alkanol is methanol.

6. The process of claim 1 or 2 wherein said N-alkylation product is N-methylaniline.

7. The process of claim 1 or 2 wherein said N-alkylation product is N,N-dimethylaniline.

8. The process of claim 1 wherein said zeolite is zeolite S-115.

9. The process of claim 1 wherein said aniline is present in relation to said lower alkanol in a molar ratio which does not exceed about 3 to 1.

10. The process of claim 5 wherein said N-alkylation product is N-methylaniline.

11. The process of claim 5 wherein said N-alkylation product is N,N-dimethylaniline.

* * * * *